United States Patent
Field

(10) Patent No.: US 9,636,082 B2
(45) Date of Patent: *May 2, 2017

(54) MEDICAL-SURGICAL DEVICES

(71) Applicant: The Cooper Companies Global Holdings LP, St. Michael (BB)

(72) Inventor: Stephen James Field, Kent (GB)

(73) Assignee: The Cooper Companies Global Holdings LP, St. Michael (BB)

( * ) Notice: Subject to any disclaimer, the term of this patent is extended or adjusted under 35 U.S.C. 154(b) by 735 days.

This patent is subject to a terminal disclaimer.

(21) Appl. No.: 13/685,865

(22) Filed: Nov. 27, 2012

(65) Prior Publication Data

US 2013/0085384 A1 Apr. 4, 2013

Related U.S. Application Data

(63) Continuation of application No. 13/064,382, filed on Mar. 22, 2011, which is a continuation of application
(Continued)

(51) Int. Cl.
*A61B 8/08* (2006.01)
*A61B 17/435* (2006.01)
(Continued)

(52) U.S. Cl.
CPC .............. *A61B 8/0841* (2013.01); *A61B 8/00* (2013.01); *A61B 8/14* (2013.01); *A61B 17/435* (2013.01);
(Continued)

(58) Field of Classification Search
CPC ........... A61B 8/0841; A61B 8/14; A61B 8/00; A61B 17/435; A61B 2090/3925;
(Continued)

(56) References Cited

U.S. PATENT DOCUMENTS 2,702,034 A 2/1955 Walter
2,740,192 A 4/1956 Ogle
(Continued)

FOREIGN PATENT DOCUMENTS

DE 38 33 365 4/1989 .......... A61M 25/098
DE 3936162 6/1991
(Continued)

OTHER PUBLICATIONS

Coloreu, B. et al., "Embryo transfer under ultrasound guidance improves pregnancy rates after in-vitro fertilization", *Human Reproduction*, vol. 15, No. 3, pp. 616-620 (2000).
(Continued)

*Primary Examiner* — Katherine M Shi
*Assistant Examiner* — Michael Mendoza
(74) *Attorney, Agent, or Firm* — Fish & Richardson P.C.

(57) ABSTRACT

An embryo replacement catheter has a flexible extruded shaft of a transparent polyurethane with a bore extending along its length. Gas bubbles of a diameter in the range 5 .mu. to 10 .mu. are incorporated into the thickness of the wall of the shaft by adding gas during extrusion. The bubbles are selected to increase the visibility of the catheter under ultrasound imaging while still enabling material flowing along the catheter to be seen. The inventive catheter is not confined to embryo replacement catheters.

30 Claims, 1 Drawing Sheet

Related U.S. Application Data

No. 10/196,151, filed on Jul. 17, 2002, now Pat. No. 8,092,390.

(51) Int. Cl.

| | | |
|---|---|---|
| *A61K 49/22* | (2006.01) | |
| *A61L 29/18* | (2006.01) | |
| *A61L 31/18* | (2006.01) | |
| *A61M 25/00* | (2006.01) | |
| *A61B 8/00* | (2006.01) | |
| *A61M 25/01* | (2006.01) | |
| *A61B 8/14* | (2006.01) | |
| *A61M 5/00* | (2006.01) | |
| *A61B 90/00* | (2016.01) | |

(52) U.S. Cl.
CPC ............ *A61K 49/223* (2013.01); *A61L 29/18* (2013.01); *A61L 31/18* (2013.01); *A61M 5/00* (2013.01); *A61M 25/007* (2013.01); *A61M 25/0009* (2013.01); *A61M 25/0012* (2013.01); *A61M 25/01* (2013.01); *A61B 2090/3925* (2016.02); *A61M 25/0043* (2013.01); *A61M 2210/1433* (2013.01)

(58) Field of Classification Search
CPC .. A61M 25/007; A61M 25/0012; A61M 5/00; A61M 25/01; A61M 25/0009; A61M 2210/1433; A61M 25/0043; A61L 29/18; A61L 31/18; A61K 49/223
USPC ................... 600/458, 461, 566, 567; 606/108
See application file for complete search history.

(56) References Cited

U.S. PATENT DOCUMENTS

| | | | |
|---|---|---|---|
| 2,989,053 | A | 6/1961 | Hamilton |
| 3,093,134 | A | 6/1963 | Roehr |
| 3,605,750 | A | 9/1971 | Sheridan et al. |
| 3,720,210 | A | 3/1973 | Diettrich |
| 4,265,251 | A | 5/1981 | Tickner |
| 4,386,628 | A | 6/1983 | Stanley |
| 4,582,061 | A | 4/1986 | Fry |
| 4,644,977 | A | 2/1987 | Arterburn |
| 4,701,161 | A | 10/1987 | Lenck |
| 4,731,052 | A | 3/1988 | Seitz, Jr. |
| 4,805,628 | A | 2/1989 | Fry et al. |
| 4,809,860 | A | 3/1989 | Allen |
| 4,810,244 | A | 3/1989 | Allen |
| 4,824,434 | A | 4/1989 | Seitz, Jr. |
| 4,832,681 | A | 5/1989 | Lenck |
| 4,869,259 | A | 9/1989 | Elkins |
| 4,874,649 | A | 10/1989 | Daubenbüchel et al. |
| 4,877,033 | A | 10/1989 | Seitz, Jr. |
| 4,887,615 | A | 12/1989 | Taylor |
| 5,048,530 | A | 9/1991 | Hurwitz |
| 5,071,425 | A | 12/1991 | Gifford, III et al. |
| 5,081,997 | A | 1/1992 | Bosley, Jr. et al. |
| 5,090,414 | A | 2/1992 | Takano |
| 5,149,328 | A | 9/1992 | Zaha |
| 5,160,319 | A | 11/1992 | Emery et al. |
| 5,195,979 | A | 3/1993 | Schinkel et al. |
| 5,201,314 | A | 4/1993 | Bosley et al. |
| 5,211,627 | A | 5/1993 | William |
| 5,250,649 | A | 10/1993 | Onwumere et al. |
| 5,259,837 | A | 11/1993 | Van Wormer |
| 5,273,527 | A | 12/1993 | Schatz et al. |
| 5,289,831 | A | 3/1994 | Bosley |
| 5,327,891 | A | 7/1994 | Rammler |
| 5,342,309 | A | 8/1994 | Hausser |
| 5,360,389 | A | 11/1994 | Chenette |
| 5,383,466 | A | 1/1995 | Partika |
| 5,405,321 | A | 4/1995 | Reeves |
| 5,415,634 | A | 5/1995 | Glynn et al. |
| 5,596,990 | A | 1/1997 | Yock et al. |
| 5,611,345 | A | 3/1997 | Hibbeln |
| 5,622,665 | A | 4/1997 | Wang |
| 5,646,194 | A | 7/1997 | Kobayashi et al. |
| 5,688,490 | A | 11/1997 | Tournier et al. |
| 5,724,977 | A | 3/1998 | Yock et al. |
| 5,741,522 | A | 4/1998 | Violante et al. |
| 5,744,092 | A | 4/1998 | Halgren et al. |
| 5,759,154 | A | 6/1998 | Hoyns |
| 5,766,135 | A | 6/1998 | Terwilliger |
| 5,769,795 | A | 6/1998 | Terwilliger |
| 5,772,642 | A | 6/1998 | Ciamacco, Jr. et al. |
| 5,820,554 | A | 10/1998 | Davis et al. |
| 5,827,174 | A | 10/1998 | Reuss, Jr. et al. |
| 5,843,023 | A | 12/1998 | Cecchi |
| 5,851,464 | A | 12/1998 | Davila et al. |
| 5,851,477 | A | 12/1998 | Halgren et al. |
| 5,879,305 | A | 3/1999 | Yock et al. |
| 5,921,933 | A | 7/1999 | Sarkis et al. |
| 5,932,154 | A | 8/1999 | Csongor et al. |
| 5,932,299 | A | 8/1999 | Katoot |
| 5,939,015 | A | 8/1999 | Csongor |
| 5,945,061 | A | 8/1999 | Csongor et al. |
| 5,967,988 | A | 10/1999 | Briscoe et al. |
| 5,976,501 | A | 11/1999 | Jablonski |
| 6,010,448 | A | 1/2000 | Thompson |
| 6,018,676 | A | 1/2000 | Davis et al. |
| 6,024,727 | A | 2/2000 | Thorne et al. |
| 6,027,443 | A | 2/2000 | Nag |
| 6,063,221 | A | 5/2000 | Weinberg et al. |
| 6,071,580 | A | 6/2000 | Bland et al. |
| 6,074,578 | A | 6/2000 | Csongor et al. |
| 6,086,540 | A | 7/2000 | Bonneville et al. |
| 6,106,473 | A | 8/2000 | Violante et al. |
| 6,110,444 | A | 8/2000 | Klaveness et al. |
| 6,165,165 | A | 12/2000 | Cecchi et al. |
| 6,207,752 | B1 | 3/2001 | Abraham et al. |
| 6,210,330 | B1 | 4/2001 | Tepper |
| 6,240,960 | B1 | 6/2001 | Fillmore |
| 6,261,241 | B1 | 7/2001 | Burbank et al. |
| 6,277,084 | B1 | 8/2001 | Abele et al. |
| 6,283,951 | B1 | 9/2001 | Flaherty et al. |
| 6,290,672 | B1 | 9/2001 | Abae |
| 6,306,094 | B1 | 10/2001 | Joseph |
| 6,312,429 | B1 | 11/2001 | Burbank et al. |
| 6,331,166 | B1 | 12/2001 | Burbank et al. |
| 6,344,026 | B1 | 2/2002 | Burbank et al. |
| 6,346,086 | B1 | 2/2002 | Maksem et al. |
| 6,347,241 | B2 | 2/2002 | Burbank et al. |
| 6,356,782 | B1 | 3/2002 | Sirimanne et al. |
| 6,358,211 | B1 | 3/2002 | Mamayek |
| 6,364,855 | B1 | 4/2002 | Zappala |
| 6,371,904 | B1 | 4/2002 | Sirimanne et al. |
| 6,371,973 | B1 | 4/2002 | Tepper |
| 6,427,081 | B1 | 7/2002 | Burbank et al. |
| 6,432,352 | B1 | 8/2002 | Csongor |
| 6,435,189 | B1 | 8/2002 | Lewis et al. |
| 6,454,727 | B1 | 9/2002 | Burbank et al. |
| 6,461,302 | B1 | 10/2002 | Thompson |
| 6,471,700 | B1 | 10/2002 | Burbank et al. |
| 6,481,462 | B2 | 11/2002 | Fillmore et al. |
| 6,497,706 | B1 | 12/2002 | Burbank et al. |
| 6,506,156 | B1 | 1/2003 | Jones et al. |
| 6,508,773 | B2 | 1/2003 | Burbank et al. |
| 6,517,498 | B1 | 2/2003 | Burbank et al. |
| 6,527,752 | B1 | 3/2003 | Bosley, Jr. et al. |
| 6,540,693 | B2 | 4/2003 | Burbank et al. |
| 6,540,695 | B1 | 4/2003 | Burbank et al. |
| 6,544,185 | B2 | 4/2003 | Montegrande |
| 6,544,230 | B1 | 4/2003 | Flaherty et al. |
| 6,567,689 | B2 | 5/2003 | Burbank et al. |
| 6,577,904 | B1 | 6/2003 | Zhang et al. |
| 6,610,005 | B1 | 8/2003 | Tao |
| 6,610,016 | B1 | 8/2003 | Violante et al. |
| 6,638,234 | B2 | 10/2003 | Burbank et al. |
| 6,656,407 | B1 | 12/2003 | Halgren et al. |
| 6,659,105 | B2 | 12/2003 | Burbank et al. |
| 6,662,041 | B2 | 12/2003 | Burbank et al. |
| 6,673,440 | B2 | 1/2004 | Douglas et al. |

(56) References Cited

U.S. PATENT DOCUMENTS

| | | |
|---|---|---|
| 6,676,658 B2 | 1/2004 | Burbank et al. |
| 6,679,824 B1 | 1/2004 | Reed et al. |
| 6,679,851 B2 | 1/2004 | Burbank et al. |
| 6,685,648 B2 | 2/2004 | Flaherty et al. |
| 6,689,071 B2 | 2/2004 | Burbank et al. |
| 6,695,767 B2 | 2/2004 | Martinez Garcia et al. |
| 6,695,787 B2 | 2/2004 | Hogendijk et al. |
| 6,699,206 B2 | 3/2004 | Burbank et al. |
| 6,712,775 B2 | 3/2004 | Burbank et al. |
| 6,716,179 B2 | 4/2004 | Burbank et al. |
| 6,723,052 B2 | 4/2004 | Mills |
| 6,725,083 B1 | 4/2004 | Burbank et al. |
| 6,736,409 B2 | 5/2004 | Hollenberg |
| 6,749,554 B1 | 6/2004 | Snow et al. |
| 6,758,848 B2 | 7/2004 | Burbank et al. |
| 6,761,680 B2 | 7/2004 | Terwilliger et al. |
| 6,786,858 B2 | 9/2004 | Terwilliger et al. |
| 6,838,278 B2 | 1/2005 | Fortino |
| 6,840,090 B2 | 1/2005 | Smith |
| 6,860,856 B2 | 3/2005 | Ward et al. |
| 6,862,470 B2 | 3/2005 | Burbank et al. |
| 6,875,168 B2 | 4/2005 | Bateman et al. |
| 6,875,182 B2 | 4/2005 | Wardle et al. |
| 6,905,458 B2 | 6/2005 | Choay et al. |
| 6,958,044 B2 | 10/2005 | Burbank et al. |
| 6,993,375 B2 | 1/2006 | Burbank et al. |
| 6,996,433 B2 | 2/2006 | Burbank et al. |
| 6,997,885 B2 | 2/2006 | Lubock et al. |
| 7,014,610 B2 | 3/2006 | Koulik |
| 7,047,063 B2 | 5/2006 | Burbank et al. |
| 7,060,020 B2 | 6/2006 | Terwilliger et al. |
| 7,188,537 B2 | 3/2007 | Junger |
| 7,189,206 B2 | 3/2007 | Quick et al. |
| 7,229,413 B2 | 6/2007 | Violante et al. |
| 7,229,418 B2 | 6/2007 | Burbank et al. |
| 7,229,439 B2 | 6/2007 | Burbank et al. |
| 7,235,052 B2 | 6/2007 | Kellar et al. |
| 7,261,712 B2 | 8/2007 | Burbank et al. |
| 7,264,596 B2 | 9/2007 | Burbank et al. |
| 7,282,034 B2 | 10/2007 | Burbank et al. |
| 7,322,938 B2 | 1/2008 | Burbank et al. |
| 7,322,939 B2 | 1/2008 | Burbank et al. |
| 7,322,940 B2 | 1/2008 | Burbank et al. |
| 7,329,228 B2 | 2/2008 | Burbank et al. |
| 7,357,794 B2 | 4/2008 | Makower et al. |
| 7,357,801 B2 | 4/2008 | Burbank et al. |
| 7,377,902 B2 | 5/2008 | Burbank et al. |
| 7,382,857 B2 | 6/2008 | Engel |
| 7,384,391 B2 | 6/2008 | Spittle et al. |
| 7,470,249 B2 | 12/2008 | Junger |
| 7,488,295 B2 | 2/2009 | Burbank et al. |
| 7,565,191 B2 | 7/2009 | Burbank et al. |
| 7,625,347 B2 | 12/2009 | Burbank et al. |
| 7,637,904 B2 | 12/2009 | Wingler et al. |
| 7,651,467 B2 | 1/2010 | Lubock et al. |
| 7,651,505 B2 | 1/2010 | Lubock et al. |
| 7,668,582 B2 | 2/2010 | Sirimanne et al. |
| 7,736,337 B2 | 6/2010 | Diep et al. |
| 7,792,569 B2 | 9/2010 | Burbank et al. |
| 7,794,402 B2 | 9/2010 | Wang |
| 7,819,819 B2 | 10/2010 | Quick et al. |
| 7,867,169 B2 | 1/2011 | Webler et al. |
| 7,879,011 B2 | 2/2011 | Chang |
| 7,887,737 B2 | 2/2011 | Mejlhede et al. |
| 7,970,454 B2 | 6/2011 | Jones et al. |
| 7,983,734 B2 | 7/2011 | Jones et al. |
| 8,052,669 B2 | 11/2011 | Lee-Sepsick et al. |
| 8,092,390 B2 | 1/2012 | Field |
| 8,137,346 B2 | 3/2012 | Burbank et al. |
| 8,147,487 B2 | 4/2012 | Burbank et al. |
| 8,152,737 B2 | 4/2012 | Burbank et al. |
| 8,177,792 B2 | 5/2012 | Lubock et al. |
| 8,200,313 B1 | 6/2012 | Rambod et al. |
| 8,219,182 B2 | 7/2012 | Burbank et al. |
| 8,224,424 B2 | 7/2012 | Burbank et al. |
| 8,229,553 B2 | 7/2012 | Burbank et al. |
| 8,273,009 B2 | 9/2012 | Arabia et al. |
| 8,282,573 B2 | 10/2012 | Shabaz et al. |
| 8,303,509 B2 | 11/2012 | Webler et al. |
| 8,306,602 B2 | 11/2012 | Sirimanne et al. |
| 8,320,993 B2 | 11/2012 | Sirimanne et al. |
| 8,320,994 B2 | 11/2012 | Sirimanne et al. |
| 8,343,071 B2 | 1/2013 | Shabaz et al. |
| 8,360,990 B2 | 1/2013 | Shabaz et al. |
| 8,361,082 B2 | 1/2013 | Jones et al. |
| 8,377,109 B2 | 2/2013 | Vrba et al. |
| 8,382,674 B2 | 2/2013 | Webler |
| 8,398,596 B2 | 3/2013 | Field |
| 8,430,863 B2 | 4/2013 | Webler |
| 8,460,204 B2 | 6/2013 | Quick et al. |
| 8,465,412 B2 | 6/2013 | Kamrava |
| 8,498,693 B2 | 7/2013 | Jones et al. |
| 8,560,052 B2 | 10/2013 | Mills |
| 8,585,596 B1 | 11/2013 | Flaherty et al. |
| 8,600,481 B2 | 12/2013 | Sirimanne et al. |
| 8,603,121 B2 | 12/2013 | Surti et al. |
| 8,622,887 B2 | 1/2014 | Gergeley |
| 8,626,269 B2 | 1/2014 | Jones et al. |
| 8,626,270 B2 | 1/2014 | Burbank et al. |
| 8,633,023 B2 | 1/2014 | Du et al. |
| 8,636,734 B2 | 1/2014 | Burbank et al. |
| 8,656,928 B2 | 2/2014 | Carlson et al. |
| 8,663,116 B2 | 3/2014 | Hamilton, Jr. |
| 8,672,892 B2 | 3/2014 | Carr et al. |
| 8,690,752 B2 | 4/2014 | Jose |
| 8,718,745 B2 | 5/2014 | Burbank et al. |
| 8,784,433 B2 | 7/2014 | Lubock et al. |
| 8,795,452 B2 | 8/2014 | Alpert et al. |
| 8,834,370 B2 | 9/2014 | Evert et al. |
| 8,880,154 B2 | 11/2014 | Jones et al. |
| 8,936,553 B2 | 1/2015 | Stigall et al. |
| 8,951,195 B2 | 2/2015 | Sheldon et al. |
| 8,959,753 B2 | 2/2015 | Garbini et al. |
| 8,965,486 B2 | 2/2015 | Burbank et al. |
| 9,033,889 B2 | 5/2015 | Hamilton, Jr. |
| 9,034,363 B2 | 5/2015 | Doshi et al. |
| 9,044,162 B2 | 6/2015 | Jones et al. |
| 9,044,215 B2 | 6/2015 | Shabaz et al. |
| 9,085,097 B2 | 7/2015 | Lentz et al. |
| 9,107,640 B2 | 8/2015 | Ho et al. |
| 9,149,341 B2 | 10/2015 | Jones et al. |
| 9,179,935 B2 | 11/2015 | Zarnescu et al. |
| 9,204,866 B2 | 12/2015 | Shabaz et al. |
| 9,216,012 B2 | 12/2015 | Burbank et al. |
| 9,216,037 B2 | 12/2015 | Buster et al. |
| 9,220,880 B2 | 12/2015 | Lee-Sepsick et al. |
| 9,237,937 B2 | 1/2016 | Burbank et al. |
| 9,242,076 B2 | 1/2016 | Burton et al. |
| 9,247,960 B2 | 2/2016 | Carson et al. |
| 9,320,540 B2 | 4/2016 | Badie |
| 2002/0026117 A1 | 2/2002 | Joseph |
| 2002/0134850 A1 | 9/2002 | Hollenberg |
| 2002/0177776 A1 | 11/2002 | Crawford Keller et al. |
| 2003/0032896 A1 | 2/2003 | Bosley et al. |
| 2003/0040756 A1 | 2/2003 | Field |
| 2003/0050531 A1 | 3/2003 | Field |
| 2003/0206864 A1 | 11/2003 | Mangin |
| 2003/0208101 A1 | 11/2003 | Cecchi |
| 2004/0230119 A1 | 11/2004 | Brustad et al. |
| 2005/0074406 A1 | 4/2005 | Couvillon, Jr. et al. |
| 2005/0143656 A1 | 6/2005 | Burbank et al. |
| 2006/0089608 A1 | 4/2006 | Shaykh et al. |
| 2006/0095015 A1 | 5/2006 | Hobbs et al. |
| 2006/0106338 A1 | 5/2006 | Chang |
| 2007/0167822 A1 | 7/2007 | Webler et al. |
| 2007/0179575 A1 | 8/2007 | Esch et al. |
| 2007/0255140 A1 | 11/2007 | Violante et al. |
| 2007/0265516 A1 | 11/2007 | Wang |
| 2008/0058702 A1 | 3/2008 | Arndt et al. |
| 2008/0154136 A1 | 6/2008 | Webler |
| 2010/0256577 A1 | 10/2010 | Field |

(56) References Cited

U.S. PATENT DOCUMENTS

| | | |
|---|---|---|
| 2010/0331955 A1 | 12/2010 | Vrba et al. |
| 2013/0281835 A1 | 10/2013 | Field et al. |

FOREIGN PATENT DOCUMENTS

| | | | |
|---|---|---|---|
| DE | 40 14 998 | 11/1991 | ............ A61M 25/01 |
| DE | 4014998 | 11/1991 | |
| DE | 299 08 256 | 7/1999 | ............... A61B 8/14 |
| DE | 197 27 740 | 9/1999 | ............... A61B 8/12 |
| EP | 0 033 659 | 8/1981 | |
| EP | 0 072 671 | 2/1983 | ............ A61B 10/00 |
| EP | 0 083 973 | 7/1983 | ............ A61B 10/00 |
| EP | 0 109 657 | 5/1984 | ............ A61M 25/00 |
| EP | 0 131 166 | 1/1985 | ............. A61M 1/00 |
| EP | 0 243 341 | 10/1987 | ............. A61M 5/14 |
| EP | 0 323 527 | 7/1989 | ............. A61M 1/00 |
| EP | 0 356 774 | 3/1990 | ............ A61M 25/00 |
| EP | 0 382 392 | 8/1990 | ............. A61B 19/00 |
| EP | 0 386 936 | 9/1990 | ............. A61B 8/08 |
| EP | 0386936 | 9/1990 | |
| EP | 0 481 685 | 4/1992 | ............. A61B 19/00 |
| EP | 0 526 669 | 2/1993 | ............ A61M 25/00 |
| EP | 0 552 924 | 7/1993 | ............. A61B 8/08 |
| EP | 0 567 285 | 10/1993 | ............ A61M 25/00 |
| EP | 0 586 056 | 3/1994 | ............ A61B 17/425 |
| EP | 0 624 342 | 11/1994 | ............. A61B 8/08 |
| EP | 0624342 | 11/1994 | |
| EP | 0 935 442 | 8/1999 | ............. A61B 8/00 |
| EP | 0 941 128 | 9/1999 | ............. A61K 49/00 |
| EP | 0 995 459 | 4/2000 | ............ A61M 25/00 |
| EP | 0 996 363 | 5/2000 | ............. A61B 8/00 |
| EP | 1 105 170 | 6/2001 | ............ A61L 31/00 |
| EP | 1 109 496 | 6/2001 | ............ A61B 10/00 |
| EP | 1 118 337 | 7/2001 | |
| EP | 1 132 049 | 9/2001 | ............. A61B 8/08 |
| EP | 1 139 878 | 10/2001 | ............ A61B 17/00 |
| EP | 1 146 910 | 10/2001 | ............. A61K 49/00 |
| EP | 1 152 696 | 11/2001 | ............ A61B 17/00 |
| EP | 1 155 418 | 11/2001 | ............... G21G 4/08 |
| EP | 1 166 720 | 1/2002 | ............ A61B 10/00 |
| EP | 1 173 096 | 1/2002 | ............. A61B 8/08 |
| EP | 1 177 776 | 2/2002 | ............. A61D 19/02 |
| EP | 1 189 546 | 3/2002 | ............. A61B 19/00 |
| EP | 1 196 107 | 4/2002 | ............. A61B 19/00 |
| EP | 1 274 353 | 1/2003 | ............ A61B 17/435 |
| EP | 1 358 856 | 11/2003 | ............. A61D 19/02 |
| EP | 1 450 891 | 9/2004 | ............. A61N 5/10 |
| EP | 1 491 147 | 12/2004 | ............ A61B 17/00 |
| EP | 1 494 721 | 1/2005 | ............. A61B 19/00 |
| EP | 1 513 581 | 3/2005 | ............ A61M 37/00 |
| EP | 1 525 856 | 4/2005 | ............. A61B 19/00 |
| EP | 1 599 125 | 11/2005 | ............ A61B 10/00 |
| EP | 1 626 667 | 2/2006 | ............. A61B 19/00 |
| EP | 1 667 589 | 6/2006 | ............. A61B 17/43 |
| EP | 1 696 800 | 9/2006 | ............ A61B 10/00 |
| EP | 1 781 178 | 5/2007 | ............ A61B 10/00 |
| EP | 1 919 388 | 5/2008 | ............ A61M 37/00 |
| EP | 1 967 147 | 9/2008 | ............ A61B 17/34 |
| EP | 2 103 266 | 9/2009 | ........... A61B 17/435 |
| EP | 2 114 270 | 11/2009 | ........... A61B 17/435 |
| EP | 2 174 596 | 4/2010 | ............ A61B 17/00 |
| EP | 2 319 449 | 5/2011 | ............ A61B 90/00 |
| EP | 2 389 868 | 11/2011 | ............ A61B 10/00 |
| EP | 2 407 111 | 1/2012 | ............ A61B 10/02 |
| EP | 2 407 119 | 1/2012 | ............ A61B 19/00 |
| EP | 2 517 630 | 10/2012 | ............. A61B 8/12 |
| EP | 2 555 687 | 2/2013 | ............ A61B 10/02 |
| EP | 2 564 890 | 3/2013 | ............ A61M 25/10 |
| EP | 2 570 150 | 3/2013 | ............ A61M 25/10 |
| EP | 2 620 111 | 7/2013 | ............ A61B 17/34 |
| EP | 2 641 546 | 9/2013 | ............ A61B 10/02 |
| EP | 2 984 991 | 2/2016 | ............ A61B 10/02 |
| EP | 2 995 260 | 3/2016 | ............ A61B 10/02 |
| FR | 2 716 266 | 8/1995 | ............ G01S 15/02 |
| GB | 829383 | 3/1960 | |
| GB | 894653 | 4/1962 | |
| GB | 1151222 | 5/1969 | ............. A61M 5/28 |
| GB | 2 263 642 | 8/1995 | ............ A61M 25/01 |
| GB | 2 274 991 | 10/1996 | |
| GB | 2 381 198 | 4/2003 | ............ A61M 25/01 |
| GB | 2 388 784 | 11/2003 | ........... A61B 17/435 |
| GB | 2 380 944 | 10/2004 | ......... A61M 25/095 |
| GB | 2 379 610 | 1/2005 | ............. A61L 29/00 |
| GB | 2494395 | 1/2014 | ............ A61M 25/10 |
| GB | 2494864 | 2/2014 | ............ A61M 25/10 |
| GB | 2469839 | 9/2014 | ............... A61B 8/00 |
| JP | 58-92951 | 6/1983 | |
| SU | 1255450 | 9/1986 | |
| WO | WO 94/17743 | 8/1994 | ........... A61B 17/435 |
| WO | 95/23615 | 9/1995 | |
| WO | WO 98/19713 | 5/1998 | |
| WO | WO 99/03399 | 1/1999 | ............... A61B 8/00 |
| WO | WO 00/09178 | 2/2000 | |
| WO | WO 02/02171 | 1/2002 | ............ A61M 25/00 |

OTHER PUBLICATIONS

Hale, Lyndon, "Embryo transfer: how to ensure correct placement in utero", *Reproduction, Fertility and Development*, vol. 13, pp. 95-98 (2001).

Strickler, Ronald C. et al., "Ultrasound guidance for human embryo transfer", *Fertility and Sterility*, vol. 43, No. 1, pp. 54-61 (Jan. 1985).

Wood, Ellen G. et al., "Ultrasound-guided soft catheter embryo transfers will improve pregnancy rates in in-vitro fertilization", *Human Reproduction*, vol. 15, No. 1, pp. 107-112 (2000).

Woolcott, Robert et al., "Potentially important variables identified by transvaginal ultrasound-guided embryo transfer", *Human Reproduction*, vol. 12, No. 5, pp. 963-966 (1997).

MEDICAL-SURGICAL DEVICES

CROSS REFERENCE TO RELATED APPLICATIONS

This application is a continuation of U.S. application Ser. No. 13/064,382, filed on Mar. 22, 2011, which is a continuation of U.S. application Ser. No. 10/196,151, filed on Jul. 17, 2002, now U.S. Pat. No. 8,092,390, which claims priority from GB application No. 0120645.7 filed on Aug. 24, 2001.

BACKGROUND OF THE INVENTION

This invention relates to medico-surgical devices.

The invention is more particularly concerned with medico-surgical devices, such as catheters, that are visible under ultrasound observation.

Ultrasound imaging equipment is increasingly being used during surgical procedures to monitor the location of a device within the body. The visibility of a device under ultrasound depends on various factors including the difference between the acoustic impedance of the material of the device and that of the surrounding medium, such as the patient tissue or body fluid within which the device is located. This difference is relatively low with plastic devices such as catheters and may make conventional catheters difficult to locate. Even devices of metal, such as needles, present problems of visibility under ultrasound observation because of the directional nature of the reflections. In some orientations a metal needle may be clearly visible but in other orientations it may be considerably less visible.

Attempts have been made to increase the visibility of medico-surgical devices under ultrasound observation in various ways. The surface of the device may be modified, such as by forming grooves or indentations in its surface. A reflective coating may be applied to the device, such as incorporating bubbles, as described in WO98/19713 and EP0624342. Alternatively, a metal marker may be secured to a plastics catheter.

BRIEF SUMMARY OF THE INVENTION

It is an object of the present invention to provide an alternative medico-surgical device.

According to one aspect of the present invention there is provided a medico-surgical device of a plastics material, the material including gas bubbles through the major part of the thickness of the material in at least a part of the device such as to increase the visibility of the device under ultrasound imaging.

The device is preferably tubular and the gas bubbles may be provided around the entire circumference of the device or may be provided in a region of the device occupying only a part of the circumference of the device, such as a strip extending along the length of the device. The outer surface of the device may be smooth and uninterrupted by gas bubbles, and the device may have an inner surface that is smooth and uninterrupted by gas bubbles. The bubbles may have a diameter in the range 1 .mu. to 50 .mu. and preferably have a diameter in the range 5 .mu. to 10 .mu. The bubbles may be substantially spherical. The device may be extruded, the gas bubbles being formed by addition of gas during extrusion of the device. Alternatively, the gas bubbles may be formed by a chemical foaming agent or by the incorporation of hollow microspheres into the plastics material. The plastics material is preferably substantially transparent, the size and density of the bubbles being selected such as to enable material flowing along the device to be viewed by the eye. The plastics material may be polyurethane.

According to another aspect of the present invention there is provided an embryo replacement catheter comprising a flexible, hollow, extruded shaft of a substantially transparent plastics material, the shaft including gas bubbles through the thickness of its wall, the density and size of the bubbles being selected to increase visibility of the catheter under ultrasound imaging whilst enabling an embryo within the catheter to be viewed by the eye, and the bore of the catheter being smooth and uninterrupted by the gas bubbles.

According to a further aspect of the present invention there is provided a method of making a medico-surgical device comprising the steps of extruding a plastics material while incorporating a gas into the wall of the device such as to form gas bubbles through the major part of the thickness of the wall of the device sufficient to increase the visibility of the device under ultrasound observation.

According to a fourth aspect of the present invention there is provided a method of making a medico-surgical device comprising forming a wall of a plastics material containing a chemical foaming agent such as to form gas bubbles through the major part of the thickness of the wall of the device sufficient to increase the visibility of the device under ultrasound observation.

According to a fifth aspect of the present invention there is provided a method of making a medico-surgical device comprising forming a wall of a plastics material containing hollow microspheres such as to form gas bubbles through the major part of the thickness of the wall of the device sufficient to increase the visibility of the device under ultrasound observation.

According to a sixth aspect of the present invention there is provided a device made by a method according to the above further aspect of the present invention.

An embryo-transfer catheter and its method of manufacture, according to the present invention, will now be described, by way of example, with reference to the accompanying drawings.

DETAILED DESCRIPTION OF THE PREFERRED EMBODIMENTS

Figure 1:
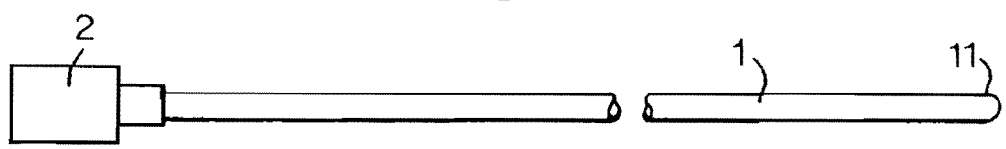
FIG. 1 is a side elevation view of the catheter.
Figure 2:
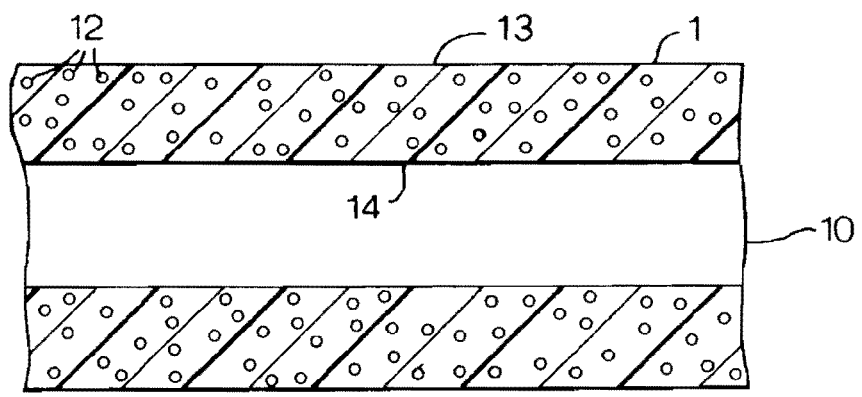
FIG. 2 is a sectional side elevation view of a part of the catheter of FIG. 1 to a larger scale.

With reference first to FIGS. 1 and 2, the catheter comprises a flexible shaft 1 and a hub 2 joined at the rear end of the shaft. The shaft 1 has a circular section and a bore 10 extending along its length. The shaft 1 opens at its forward, right-hand, patient end 11, which is atraumatically rounded. The shaft 1 is extruded from a clear, transparent polyurethane material and incorporates small, gas-filled bubbles 12 the size and distribution of which are selected to increase the visibility of the catheter under ultrasound observation. Typically, the gas bubbles have a diameter in the range of about 0.1 .mu. to 300 .mu., preferably being between 1 .mu. and 50 .mu. with the most preferred range being 5 .mu. to 10 .mu. The bubbles 12 extend through the entire thickness of the wall of the shaft 1 and may be spherical or of any other regular or irregular shape. The outer and inner surfaces 13 and 14 of the shaft may be smooth and uninterrupted by gas bubbles or the bubbles may break the surface.

The hub 2 serves to make connection with the shaft 1 and is moulded from a rigid, transparent plastics material, being subsequently bonded with the rear end of the shaft.

Figure 3:
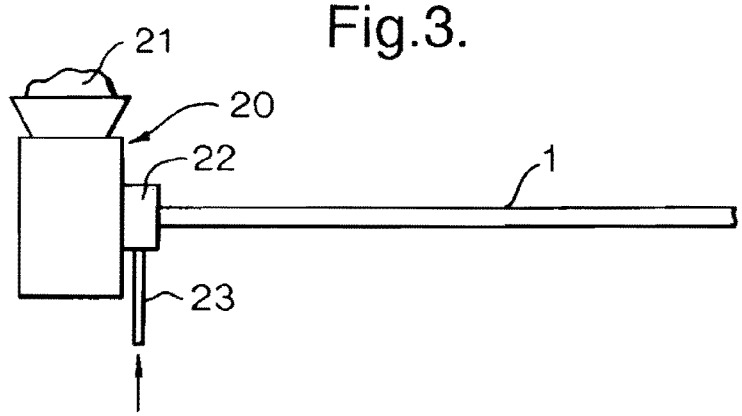
FIG. 3 illustrates schematically manufacture of the catheter.

The shaft 1 is extruded in the manner shown in FIG. 3 using an extrusion machine 20. Polyurethane material 21 is heated and supplied to the extrusion head 22 in the usual way but a gas such as nitrogen of carbon dioxide is also injected through the inlet 23 under pressure into the melt. As the plastics emerges from the extrusion head 22 the gas expands to form the bubbles 12. The relatively gas-permeable nature of the plastics means that after manufacture the bubble-forming gas will quickly escape and be replaced with air.

The shaft 1 can be extruded continuously at low cost, without the need for any subsequent operations apart from attaching the hub 2 and end forming the patient end tip 11.

The catheter shaft could be formed by other melt processes, such as injection moulding or blow moulding.

The bubbles could be formed in ways other than by injection of gas into the melt. For example, chemical foaming agents could be added to the plastics material, such as: azocarbonomides, dinitrosopentmethelyene-tetramine, benzenephonohydrazine, 4,4 oxybis(benzenephonohydrazine), NN.sup.1dimethyl-NN.sup.1 dinitrosoterephthalamide, azoisobutyronitrile, sodium bicarbonate, terephthalazide or trihydrazinatrazine. Another way of forming the gas bubbles would be by incorporating a liquid into the plastics melt which volatises during the melt process. Alternatively, solid powdered dry ice (carbon dioxide) could be incorporated into the melt so that the particles of dry ice become gas bubbles during the forming process. It might be possible to use other solids which undergo sublimation in this way. The bubbles could be formed directly as a result of chemical reaction during polymerisation and or alternatively during cross-linking. The bubbles could be formed mechanically by whipping the plastics in a liquid form, such as in the manner used to form latex foam. The bubbles could be formed by the incorporation of hollow microspheres of resin or glass. Alternatively, small particles of a soluble material could be added to the plastics melt and subsequently dissolved away.

A shaft of this kind can have good visibility under ultrasound imaging without producing multiple echoes and can produce a good image regardless of the orientation of the shaft. The shaft can be made sufficiently transparent to ultrasound energy to enable material flowing along the bore of the catheter to be observed on the ultrasound image.

Because the catheter does not require any coating or separate marker there is no need for subsequent assembly operations and there is no risk of detachment. The catheter can be made of conventional medically-approved materials so does not present any new risk to the patient. Because the surface of the catheter can be smooth, the catheter can be inserted or slid through an outer tube with low friction. The smooth bore of the catheter ensures free flow along the bore, which can be important where the catheter is used to transfer embryos. The smooth surfaces also reduce the accumulation of biofilm on the catheter. The catheter can be made without the need for metal components, which can be an advantage where the catheter is used while the patient is being viewed by magnetic imaging techniques. The catheter can be completely transparent to x-rays or the plastics from which it is formed could incorporate an x-ray opaque filler, such as barium sulphate.

The bubble size and density can be selected so that the optical transparency of the plastics forming the shaft remains sufficient to enable material flowing along the shaft to be viewed by the eye.

There are various ways in which the catheter could be modified. For example, it could be preferable for the bubbles to have a non-spherical shape and be oriented in a particular direction, such as longitudinally. This could be achieved by means of an obstruction in the extrusion die that constricts and elongates the bubbles as they flow through. Such an arrangement may give an increase in ultrasound visibility whilst reducing the opacity of the shaft to the eye.

Figure 4:
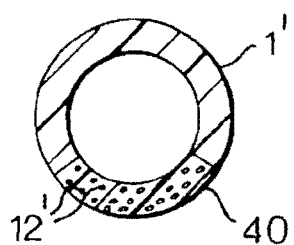
FIG. 4 is a sectional transverse view through an alternative catheter.

It is not essential for the bubbles to be provided around the entire circumference of the shaft. As shown in FIG. 4, the bubbles 12' could be formed only in one or more stripes extending along the shaft 1', such as in the stripe 40. This arrangement can be used where the shaft needs to have increased clarity so that material within the catheter can be seen by the eye. The bubble region need not be continuous along the length of the catheter. Instead, discrete separate regions with bubbles could be separated from one another along the length of the catheter by regions without bubbles. A shaft for such a catheter could be made by interrupting gas flow to the extruder. Where the bubbles are contained within a stripe, this could be interrupted to make it discontinuous by extruding the stripe using two auxiliary extruders, one having material with a blowing agent and the other having material without the blowing agent. Alternate extruders are switched on and off so that the stripe can have sections containing bubbles separated from one another by sections without bubbles. A catheter with an interrupted bubble region may give a clearer ultrasound indication of movement of the catheter along its length and may also enable clearer observation of material flowing along the catheter both by ultrasound and by the eye.

The invention claimed is:

1. A medical surgical device with a shaft made of plastics material, the shaft having a bore defined by a circular smooth inner surface, the bore extending along the length of the shaft, the shaft including a wall having a thickness defined between the inner surface and a concentric outer surface, gas bubbles being incorporated into and distributed in at least one region of the wall of the shaft between the inner and outer surfaces and having a size selected to increase the visibility of the shaft under ultrasound observation, the increase in the visibility of the shaft under ultrasound observation resulting only from the incorporation of the gas bubbles into the wall of the shaft.

2. The device of claim 1, wherein the wall of the shaft consists of the plastics material and the gas bubbles incorporated and distributed therein.

3. The device of claim 1, wherein the gas bubbles are distributed throughout the thickness of the wall along the length of the shaft.

4. The device of claim 1, wherein the gas bubbles are formed in the wall of the shaft by the incorporation of hollow microspheres into the plastics material.

5. The device of claim 1, wherein the gas bubbles are formed in the wall of the shaft by the adding of particles of a soluble material to a plastics melt used in forming the shaft.

6. The device of claim 1, wherein the shaft is made by extrusion.

7. The device of claim 1, wherein the shaft is made to be substantially transparent to ultrasound energy so as to enable material flowing along the bore of the shaft to be viewed by eye.

8. The device of claim 1, wherein the device is an embryo replacement catheter where the passage of an embryo flowing along the catheter is viewable under ultrasound observation.

9. The device of claim 1, wherein the gas bubbles have diameters in the range 1 .mu. to 50 .mu., and preferably in the range 5 .mu. to 10 .mu.

10. The device of claim 1, wherein the gas bubbles may be spherical or of irregular shape.

11. The device of claim 1, wherein the gas bubbles are formed in the wall of the shaft by adding a chemical foaming agent to the plastics material.

12. A catheter including a circular shaft having a wall made of a plastics material defined between an inner surface and an outer surface, the circular inner surface defining a bore extending along the length of the shaft, the shaft consisting of the plastics material and gas bubbles of a selected size incorporated throughout the thickness of the wall at at least one region of the shaft, wherein the visibility of the shaft under ultrasound observation is increased due to the gas bubbles having been incorporated throughout the wall of the shaft.

13. The catheter of claim 12, wherein the gas bubbles are distributed throughout the thickness of the wall along the length of the shaft.

14. The catheter of claim 12, wherein the gas bubbles are formed in the wall of the shaft by the incorporation of hollow microspheres into the plastics material.

15. The catheter of claim 12, wherein the shaft is formed by extrusion from a plastics melt using an extrusion machine, and wherein the gas bubbles are formed by injecting a gas into the melt.

16. The catheter of claim 12, wherein the gas bubbles are formed from particles of a soluble material added to a plastics melt used for forming the shaft.

17. The catheter of claim 12, wherein the shaft is made to be substantially transparent to ultrasound energy so as to enable material flowing along the bore of the shaft to be viewed by eye.

18. The catheter of claim 12, wherein the catheter is an embryo replacement catheter.

19. The catheter of claim 12, wherein the gas bubbles are formed in the wall of the shaft by adding a chemical foaming agent to the plastics material.

20. A method of making a medical surgical device comprising forming a shaft of plastics material having a through bore extending along its length with a wall having a thickness defined by a smooth inner surface and an outer surface, and incorporating gas bubbles that have a selected size in at least one region of the wall of the shaft, wherein the visibility of the shaft under ultrasound observation is increased only due to the incorporation of the gas bubbles into the wall of the shaft.

21. The method of claim 20, wherein the gas bubbles are distributed throughout the wall of the shaft.

22. The method of claim 20, wherein the gas bubbles are formed in the wall of the shaft by the incorporation of hollow microspheres into the plastics material.

23. The method of claim 20, wherein the gas bubbles are formed in the wall of the shaft by injecting gas into the plastics material as the shaft is being molded or extruded from the plastics material.

24. The method of claim 20, forming the shaft to be substantially transparent to ultrasound energy so as to enable material flowing along the bore of the shaft to be viewed by eye.

25. The method of claim 20, wherein the gas bubbles are formed in the wall of the shaft by adding a chemical foaming agent to the plastics material.

26. A method of increasing the visibility of a catheter having a shaft made of a plastics material and having a wall defined between concentric inner and outer surfaces, the inner surface defining a through bore extending along the shaft, the method comprising incorporating gas bubbles with a selected size to increase the visibility of the plastics material in the wall of the shaft as the shaft is being formed or extruded so that the visibility of the shaft under ultrasound observation is increased only due to the gas bubbles having been incorporated into the wall of the shaft.

27. The method of claim 26, wherein the gas bubbles are distributed throughout the wall of the shaft.

28. The method of claim 26, wherein the gas bubbles are formed in the wall of the shaft by the incorporation of hollow microspheres into the plastics material.

29. The method of claim 26, wherein the gas bubbles are formed in the wall of the shaft by injecting gas into the plastics material as the shaft is being molded or extruded from the plastics material.

30. The method of claim 26, wherein the gas bubbles are formed in the wall of the shaft by adding a chemical foaming agent to the plastics material.

\* \* \* \* \*

UNITED STATES PATENT AND TRADEMARK OFFICE
CERTIFICATE OF CORRECTION

PATENT NO. : 9,636,082 B2 Page 1 of 1
APPLICATION NO. : 13/685865
DATED : May 2, 2017
INVENTOR(S) : Stephen James Field et al.

It is certified that error appears in the above-identified patent and that said Letters Patent is hereby corrected as shown below:

On the Title Page

Page 2
Column 1, Line 3, after "8,092,390" insert:
-- (30) Foreign Application Priority Data
Aug. 24, 2001   (GB) ............ 0120645.7 --

Signed and Sealed this
Twenty-seventh Day of June, 2017

Joseph Matal
*Performing the Functions and Duties of the*
*Under Secretary of Commerce for Intellectual Property and*
*Director of the United States Patent and Trademark Office*